US005614210A

United States Patent [19]
Braun

[11] Patent Number: 5,614,210
[45] Date of Patent: Mar. 25, 1997

[54] TRANSDERMAL DEVICE FOR THE DELIVERY OF ALFUZOSIN

[75] Inventor: Franz-Josef Braun, Borken, Germany

[73] Assignee: Minnesota Mining and Manufacturing Company, St. Paul, Minn.

[21] Appl. No.: 414,188

[22] Filed: Mar. 31, 1995

[51] Int. Cl.$^6$ ............................................. A61F 13/02
[52] U.S. Cl. ............................. 424/448; 424/449
[58] Field of Search ................................. 429/448, 449

[56] References Cited

U.S. PATENT DOCUMENTS

| | | | |
|---|---|---|---|
| Re. 24,906 | 12/1960 | Ulrich | 206/59 |
| 3,786,116 | 1/1974 | Milkovich et al. | 260/885 |
| 3,842,059 | 10/1974 | Milkovich et al. | 260/93.5 A |
| 4,732,808 | 3/1988 | Krampe et al. | 428/355 |
| 4,737,559 | 4/1988 | Kellen et al. | 526/291 |
| 5,523,094 | 6/1996 | Andrieu | 424/449 |

FOREIGN PATENT DOCUMENTS

| | | |
|---|---|---|
| 0582502 | 7/1993 | European Pat. Off. . |
| 92/14453 | 9/1992 | WIPO . |

OTHER PUBLICATIONS

Schulz et al., "Functionally Terminal Polymers via Anionic Methods", *Anionic Polymerization*, American Chemical Society, vol. 166, pp. 427–440 (1981).

*Primary Examiner*—D. Gabrielle Phelan
*Attorney, Agent, or Firm*—Gary L. Griswold; Walter N. Kirn; Ted K. Ringsred

[57] ABSTRACT

A transdermal drug delivery device involving an acrylate or methacrylate based adhesive copolymer, a skin penetration enhancer, and a therapeutically effective amount of alfuzosin.

20 Claims, No Drawings

TRANSDERMAL DEVICE FOR THE DELIVERY OF ALFUZOSIN

BACKGROUND OF THE INVENTION

1. Field of the Invention

This invention relates to transdermal drug delivery devices. In another aspect this invention relates to pharmaceutical formulations containing alfuzosin.

2. Description of the Related Art

Transdermal drug delivery devices are designed to deliver a therapeutically effective amount of drug across the skin of a patient. Devices known to the art include reservoir type devices involving membranes that control the rate of drug release to the skin and devices involving a dispersion of the drug in a matrix such as a pressure sensitive adhesive. The skin, however, presents a substantial barrier to ingress of foreign substances into the body. It is therefore often desirable or necessary to incorporate certain materials that enhance the rate at which the drug passes through the skin. However, the type of device, the transdermal flux rate that is suitable, and the suitable formulation components are dependent upon the particular drug to be delivered.

Alfuzosin, N-[3-[(4-amino-6,7-dimethoxy-2-quinazolinyl)methylamino]propyl]tetrahydro-2-furancarboxamide, is a selective $\alpha_1$-adrenoreceptor antagonist. It has been administered as the hydrochloride salt for the treatment of urinary obstruction caused by benign prostatic hypertrophy. It has also been evaluated for the treatment of hypertension.

SUMMARY OF THE INVENTION

This invention provides a transdermal delivery device comprising:

(A) a backing;
(B) an adhesive layer adhered to one surface of the backing and comprising a combination of
  (1) a copolymer comprising
    (a) one or more A monomers selected from the group consisting of alkyl acrylates containing 4 to 10 carbon atoms in the alkyl group and alkyl methacrylates containing 4 to 10 carbon atoms in the alkyl group; and
    (b) one or more ethylenically unsaturated B monomers comprising a functional group selected from the group consisting of carboxylic acid, sulfonamide, urea, carbamate, carboxamide, hydroxy, amino, oxy, oxo, and cyano;
  (2) alfuzosin in an amount effective as an $\alpha_1$-adrenoreceptor antagonist;
  (3) a skin-penetration enhancing amount of a fatty compound selected from the group consisting of $C_8$–$C_{22}$ fatty acids, lower alkyl esters of $C_8$–$C_{22}$ fatty acids, and mixtures thereof.

DETAILED DESCRIPTION OF THE INVENTION

The term "lower alkyl" as used herein means straight chain or branched chain alkyl containing 1 to 4 carbon atoms.

This invention provides transdermal drug delivery devices containing alfuzosin. The alfuzosin is present in a therapeutically effective amount, i.e., an amount effective to bring about a desired therapeutic result in the treatment of a condition and in any event an amount effective as a $\alpha_1$-adrenoreceptor antagonist. The amount that constitutes a therapeutically effective amount varies according to the condition being treated (e.g., urinary obstruction caused by benign prostatic hypertrophy, hypertension), any drugs being coadministered with alfuzosin, desired duration of treatment, the surface area of the skin over which the device is to be placed, and other components of the transdermal delivery device. Accordingly it is not practical to enumerate particular preferred amounts but such can be readily determined by those skilled in the art with due consideration of these factors. Generally, however, alfuzosin is present in a device of the invention in an amount of about 20 to about 40 percent, preferably about 25 to 35 percent, by weight based on the total weight of the adhesive layer. A device of the invention preferably contains a therapeutically effective amount of alfuzosin dissolved in the adhesive layer, and more preferably the adhesive layer is substantially free of solid undissolved alfuzosin.

The adhesive layer contains a copolymer as defined above, alfuzosin, an adjuvant as defined above, and any other necessary or desirable excipients, preferably as a substantially homogeneous combination (i.e., a dispersion wherein the dispersed components are substantially uniformly distributed throughout the adhesive layer bulk, or a solution). The adhesive layer in a device of the invention is generally about 25–600 µm thick. It can be adhered to a backing directly or via an intermediate layer.

The copolymer utilized in the practice of the invention should be substantially chemically inert to alfuzosin. The inherent viscosity of the copolymer is such as to ultimately provide a suitable pressure sensitive adhesive when used in a device of the invention. Preferably the copolymer has an inherent viscosity in the range 0.2 dl/g to about 2 dl/g, more preferably 0.3 dl/g to about 1.4 dl/g.

Suitable copolymers for use in an adhesive layer preferably comprise about 45 to 95 percent by weight, more preferably 55 to 95 percent by weight, based on the total weight of all monomers in the copolymer, of one or more A monomers selected from the group consisting of alkyl acrylates containing 4 to 10 carbon atoms in the alkyl group and alkyl methacrylates containing 4 to 10 carbon atoms in the alkyl group. Examples of suitable alkyl acrylates and methacrylates are n-butyl, n-pentyl, n-hexyl, isoheptyl, n-nonyl, n-decyl, isohexyl, 2-ethyloctyl, isooctyl and 2-ethylhexyl acrylates and methacrylates. Preferred alkyl acrylates include isooctyl acrylate, 2-ethylhexyl acrylate, n-butyl acrylate, and cyclohexyl acrylate. The most preferred alkyl acrylate is isooctyl acrylate. Preferred alkyl methacrylates include butyl methacrylate, cyclohexyl methacrylate, and isobornyl methacrylate.

The copolymer component of the adhesive layer further comprises one or more ethylenically unsaturated B monomers, preferably in a total amount from about 5 to 55 percent by weight, more preferably greater than 5 to about 40 percent by weight (based on the total weight of all the monomers in the copolymer). Suitable B monomers include those comprising a functional group selected from the group consisting of carboxylic acid, sulfonamide, urea, carbamate, carboxamide, hydroxy, amino, oxy, oxo, and cyano. Exemplary B monomers include acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, diacetone acrylamide, a dialkyl acrylamide having 1 or 2 carbon atoms in the alkyl group, N-vinyl-N-methyl acetamide, N-vinyl valerolactam, N-vinyl caprolactam, N-vinyl-2-pyrrolidone, glycidyl methacrylate, vinyl acetate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl methacrylate, furfuryl acrylate, tetrahydrofurfuryl acrylate, tetrahydrofurfuryl methacrylate, propylene glycol monomethacrylate, polyethylene oxide methyl ether acrylates, polyethylene glycol methyl ether acrylates, di(lower)alkylamino ethyl acrylate, di(lower)alkylamino ethyl methacrylate, di(lower)alkylaminopropyl methacrylamide, acrylonitrile, and methacrylonitrile.

The preferred B monomers include hydroxyethyl acrylate, hydroxyethyl methacrylate, glyceryl acrylate, N,N-dimethyl acrylamide, 2-ethoxyethoxyethyl acrylate, 2-ethoxyethyl acrylate, tetrahydrofurfuryl acrylate, acrylamide, vinyl acetate, and acrylic acid. Most preferred B monomers include hydroxyethyl acrylate, N,N-dimethyl acrylamide, acrylic acid, acrylamide, vinyl acetate, and a combination thereof.

The adhesive layer further comprises a fatty compound selected from the group consisting of: $C_8$–$C_{22}$ fatty acids, including saturated fatty acids such as caprylic acid, lauric acid, myristic acid, palmitic acid, stearic acid, and isostearic acid, and unsaturated fatty acids such as oleic acid and linoleic acid; and $C_1$–$C_4$ alkyl esters of the above, such as methyl, ethyl, and isopropyl esters, including isopropyl myristate, ethyl oleate, and methyl laurate, and a combination of any one or more of any of the foregoing. Preferred compounds include isopropyl myristate, lauric acid, and caprylic acid.

In a device of the invention the fatty compound is dispersed, preferably substantially uniformly dispersed, and more preferably dissolved in the adhesive layer and is present in an amount that enhances alfuzosin penetration through the skin compared to a like device not containing the fatty compound when this phenomenon is measured using the skin penetration model described below.

Fatty compounds, however, can affect aspects of performance of a transdermal device other than and in addition to drug penetration rate. For example, they can soften or increase the compliance value and/or lower the glass transition temperature of otherwise non-compliant (and therefore relatively poorly pressure sensitive adhesive) copolymers, rendering them suitable for use as pressure sensitive skin adhesives. However, the fatty compounds enumerated above are generally oily substances that function as plasticizers when incorporated in a copolymer. Such materials can affect adversely the adhesive performance of a copolymer, for example by softening it to the point of cohesive failure (where substantial residue is left on the skin upon removal of the device from the skin) or by separating from the continuous phase of the layer and forming an oily layer that reduces adhesion.

Possible adverse effects of fatty compounds notwithstanding, in the practice of this invention fatty compound amounts in excess of 20% and less than about 40% by weight based on the total weight of the adhesive layer have been found to be preferred, and amounts in excess of 30% are more preferred. With proper selection of fatty compounds, monomers and relative amounts thereof, and inherent viscosity of the copolymer, fatty compounds can be included in amounts of up to about 40% by weight based on the total weight of the adhesive layer without cohesive failure or phase separation, and without loss of suitable skin adhesion.

It has been found that certain transdermal drug delivery devices containing alfuzosin and the fatty compounds described above can be irritating to skin. Therefore the adhesive layer optionally further comprises glycerin. If it is used, glycerin is preferably present in an amount effective to mitigate skin irritation. The amount that constitutes such an effective amount is variable depending upon the alfuzosin concentration, the fatty compound concentration, the particular subjects to which the ultimate device is applied, and the intended duration of adhesion. Generally amounts from about 0.01% to about 10% by weight based on the total weight of the adhesive layer are suitable.

In order to accommodate high loading with fatty compounds and/or glycerin it is sometimes preferred to incorporate in the copolymer a substantially linear macromonomer copolymerizable with the A and B monomers defined above and having a molecular weight in the range 500–500,000, preferably 2,000–100,000, and more preferably 5,000–30,000, in an amount (e.g., at least about 0.1 percent by weight based on the total weight of comonomers in the copolymer) effective to control the rheological properties of the copolymer such that when borne upon a backing the adhesive layer maintains intimate contact with the skin when applied by hand and does not leave substantial residue on the skin when peeled from the skin. The macromonomer, when used, is generally present in an amount of not more than about 30%, more preferably not more than 20%, even more preferably not more than about 15%, and most preferably not more than about 10%, by weight based on the total weight of all monomers in the copolymer.

The macromonomer can be a compound of the formula

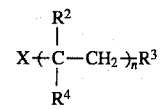

wherein X is a moiety comprising an ethylenically unsaturated group (e.g., —CH═C(CH$_3$)(CO$_2$CH$_3$),

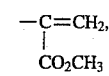

vinyl, or 2-propenyl) copolymerizable with the A and B monomers, $R^2$ is a hydrogen atom or a lower alkyl group, $R^3$ is a lower alkyl group, n is an integer from 20 to 500 and each $R^4$ is a monovalent radical selected from the group consisting of

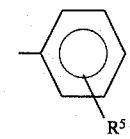

—CN, and —CO$_2$R$^6$ wherein $R^5$ is a hydrogen atom or a lower alkyl group, and $R^6$ is a lower alkyl group. Suitable macromonomers include polymethylmethacrylate, styrene/acrylonitrile, and polystyrene macromonomers. Polymethylmethacrylate macromonomers are preferred.

Exemplary macromonomers include those having a general formula selected from the group consisting of

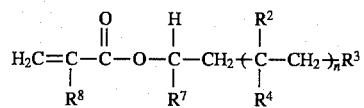

-continued

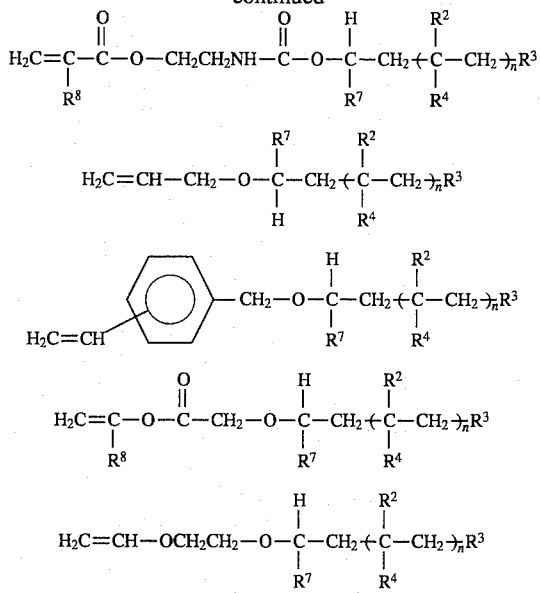

wherein $R^7$ is a hydrogen atom or a lower alkyl group, $R^8$ is hydrogen or methyl, and $R^2$, $R^3$, and $R^4$ are as defined above.

The macromonomers shown in the formulae directly above are functionally terminated polymers having a single functional group and are sometimes identified as "semitelechelic" polymers. (Vol. 27 "Functionally Terminal Polymers via Anionic Methods" D. N. Schultz et al., pages 427–440, *Anionic Polymerization*, American Chemical Society (1981)). Such macromonomers are known and may be prepared by the method disclosed in U.S. Pat. Nos. 3,786,116, 3,842,059 (both to Milkovich et al.), and 4,732,808 (Krampe et al.), the disclosures of which are incorporated herein by reference for the description of the preparation of the macromonomers. Certain macromonomers are commercially available, for example those polymethylmethacrylate macromonomers sold under the trade designation "ELVACITE" by ICI Acrylics (e.g., ELVACITE 1010, a polymethylmethacrylate macromonomer having an inherent viscosity of 0.070–0.080, a $T_g$ of 105° C., a GPC weight average molecular weight of 7,000–10,000, a GPC number average molecular weight of 2,500–4,000, and a polydispersity of 2.5–3.0, and ELVACITE 1020, a polymethylmethacrylate macromonomer having an inherent viscosity of 0.085–0.10, a $T_g$ of 105° C., a GPC weight average molecular weight of 12,000–15,000, a GPC number average molecular weight of 4,600–6,000, and a polydispersity of 2.5–3.0).

The properties desirable in a transdermal device are well known to those skilled in the art. For example, it is desirable for an adhesive layer to have sufficiently little cold flow such that a device of the invention is stable to flow upon storage. It is also preferred that it adhere to the skin and release cleanly from the skin. In order to achieve skin contact, clean release, and preferred levels of skin adhesion and resistance to cold flow, the amount and structure of the comonomers in the copolymer, the inherent viscosity of the copolymer, and the amount and structure of the fatty compounds are selected such that the device has a compliance value of $1 \times 10^{-5}$ to $5 \times 10^{-4}$ cm$^2$/dyne (compliance values can be determined using the Creep Compliance Procedure described in U.S. Pat. No. 4,737,559 (Kellen), the disclosure of which is incorporated herein by reference). Compliance values outside this range sometimes are obtained from materials that are suitable. However, those adhesive layers having substantially lower compliance values will generally be relatively stiff and have less than optimal adhesion to skin. Those having substantially higher compliance values will generally have less than optimal cold flow and might leave substantial residual matrix when removed from the skin. Also, an adhesive layer preferably has a glass transition temperature of −10° C. or lower.

Particularly suitable compositions can be readily selected for a given set of desired properties considering the effects of comonomers, inherent viscosity, and fatty compounds on the properties of the resulting composition. Certain of such effects are well known to those skilled in the art, and others are described below:

Strongly hydrogen bonding B monomers have been found to decrease the amount of fatty compound that can be dissolved in an adhesive layer. Further, a strongly hydrogen bonding copolymer will be a relatively less compliant material. Therefore if B monomers such as acrylic acid or acrylamide are used a lesser amount of macromonomer (or none at all) will be required in order to lower compliance sufficiently to avoid cohesive failure.

Macromonomers also decrease compliance. Therefore a given target compliance value can often be achieved using a lower inherent viscosity A/B copolymer combination and a greater amount of macromonomer, or a higher inherent viscosity A/B combination and less macromonomer.

A relatively high compliance pressure sensitive skin adhesive layer involving a macromonomer will generally have better adhesive properties than an A/B copolymer having the same compliance value. Increasing macromonomer content generally increases the amount of fatty compound that can be loaded into a pressure sensitive skin adhesive without cohesive failure. Increasing inherent viscosity will also tend to allow higher loading without cohesive failure.

A change that would increase inherent viscosity of a copolymer (such as increased molecular weight through selection of polymerization conditions and/or solvent ratios) will generally decrease compliance.

Further conventional components, such as stabilizers and reinforcers (e.g., colloidal silicon dioxide), can be incorporated into the adhesive layer if necessary or desirable.

An adhesive layer in a device of the invention preferably contains less than about 4 percent by weight of water based on the total weight of the adhesive layer. More preferably it is substantially free of water (i.e., it contains no water in addition to that incidentally present in the various components of the adhesive layer).

A transdermal delivery device of the invention also comprises a backing. The backing is flexible such that the device conforms to the skin. Suitable backing materials include conventional flexible backing materials used for pressure sensitive tapes, such as polyethylene, particularly low density polyethylene, linear low density polyethylene, high density polyethylene, polyester, polyethylene terephthalate, randomly oriented nylon fibers, polypropylene, ethylenevinyl acetate copolymer, polyurethane, rayon and the like. Backings that are layered, such as polyethylene-aluminum-polyethylene composites, are also suitable. The backing should be substantially inert to the ingredients of the adhesive layer.

The adhesive copolymers described above for use in a device of the invention can be prepared by methods well known to those skilled in the art and described, for example, in U.S. Pat. RE No. 24,906 (Ulrich) and U.S. Pat. No. 4,732,808 (Krampe at al.), the disclosures of which are incorporated herein by reference.

Transdermal delivery devices of the invention are preferably prepared by combining the copolymer, the desired fatty compounds, the glycerin (if any), and the alfuzosin with an organic solvent (e.g., ethyl acetate, methanol, acetone, 2-butanone, ethanol, isopropyl alcohol, toluene, alkanes, and mixtures thereof) to afford a coating formulation. The total solids content of the coating formulation is preferably in a range of about 15 to 50 percent by weight, and more preferably in the range of about 25 to 45 percent by weight, based on the total weight of the coating formulation. The components of the coating formulation are combined and shaken at high speed until a homogeneous formulation is obtained, then allowed to stand to dissipate air bubbles. The resulting coating formulation is knife coated onto a suitable release liner to provide a predetermined uniform thickness of the coating formulation. Suitable release liners include conventional release liners comprising a known sheet material such as a polyester web, a polyethylene web, or a polystyrene web, or a polyethylene-coated paper, coated with a suitable fluoropolymer or silicone based coating. The coated release liner is dried and then laminated onto a backing material using conventional methods.

The transdermal delivery devices of the invention can be made in the form of an article such as a tape, a patch, a sheet, a dressing or any other form known to those skilled in the art. Generally the device will be in the form of a patch of a size suitable to deliver a preselected amount of alfuzosin through the skin. Generally the device will have a surface area of about 10 cm$^2$ to about 40 cm$^2$.

A device of the invention can be used to treat any condition capable of treatment with alfuzosin. The device can be placed on the skin and allowed to remain for a time sufficient to achieve or maintain the intended therapeutic effect. The time that constitutes a sufficient time can be selected by those skilled in the art with consideration of the flux rate of the device of the invention and upon the condition being treated.

The examples set forth below are intended to illustrate the invention.

In Vitro Skin Penetration Test Method

The skin penetration data given in the examples below was obtained using the following test method. A diffusion cell is used. Hairless mouse skin (female hairless mice, 3–4 weeks old) is mounted epidermal side up between the upper portion and the lower portion of the cell, which are held together by means of a ball joint clamp.

The portion of the cell below the mounted skin is completely filled with receptor fluid (McIlvaine buffer solution, pH 6.8 prepared by combining 1544 mL of 0.25M dibasic sodium phosphate with 456 mL of 0.1M citric acid then adjusting to pH 6.8 using 1N sodium hydroxide or 1N hydrochloric acid) such that the receptor fluid is in contact with the skin. The receptor fluid is stirred using a magnetic stirrer. The sampling port is covered except when in use.

When a transdermal delivery device is evaluated, the skin is placed across the orifice of the lower portion of the diffusion cell, the release liner is removed from a 1.55 cm$^2$ patch and the patch is applied to the skin and pressed to cause uniform contact with the skin. The diffusion cell is assembled and the lower portion is filled with warm (32° C.) receptor fluid.

The cell is then placed in a constant temperature (32°±2° C.) and humidity (50±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals (3, 6, 12, 24 and 48 hours) and immediately replaced with fresh fluid. A 1 mL portion of the withdrawn fluid is diluted with 4 mL of mobile phase. A 20 µL portion of the resulting solution is then analyzed for alfuzosin using high performance liquid chromatography (Column: 15 cm×4.6 mm I.D. Inertsil ODS II/5 µM from Optilab; Mobile phase: 25/75 v/v acetonitrile/perchloric acid buffer solution (Prepared by combining 5 mL perchloric acid with 900 mL water, adjusting the pH to 6.5 with 2N sodium hydroxide and then bringing the final volume to 1 L with additional water.); Flow rate: 1.5 mL/min; Run Time: 8 minutes; Detection: uv at 254 nm). The cumulative amount of alfuzosin penetrating the skin is calculated. Plots of the cumulative alfuzosin penetration as a function of time give a profile of the alfuzosin flux measured in µg/cm$^2$/hour.

Preparation of Adhesive Copolymers

The adhesive copolymers used in the examples that follow were prepared generally according to the methods described below. The inherent viscosity values which are reported were measured by conventional means using a Cannon-Fenske #50 viscometer in a water bath controlled at 27° C. to measure the flow time of 10 mL of a polymer solution (0.15–0.25 g per deciliter of polymer in ethyl acetate, unless otherwise indicated). The test procedure followed and the apparatus used are described in detail in "Textbook of Polymer Science", F. W. Billmeyer, Wiley-Interscience, Second Edition, 1971, p. 84–85.

Preparation of Isooctyl Acrylate/Acrylamide/Vinyl Acetate (75/5/20) Copolymer

A master batch was prepared by combining isooctyl acrylate (621.0 g), acrylamide (41.4 g), vinyl acetate (165.6 g), 2,2'azobis(2,4-dimethylpentanenitrile) (1.656 g, VAZO™ 52, DuPont), ethyl acetate (884.5 g) and methanol (87.48 g). A portion (400 g) of the resulting solution was placed in a one quart (0.95 L) amber glass bottle. The bottle was purged for 2 minutes with nitrogen at a flow rate of 1 L/min. The bottle was sealed and placed in a rotary water bath at 45° C. for 24 hours to effect essentially complete polymerization. The copolymer was diluted with ethyl acetate: methanol (90:10 v/v) to 26.05% solids and had an inherent viscosity of 1.27 deciliter/gram in ethyl acetate at 0.15 g/deciliter.

Preparation of Isooctyl Acrylate/Hydroxyethyl Acrylate/Polymethylmethacrylate Macromonomer (57/38/5) Copolymer Isooctyl acrylate (142.5 g), hydroxyethyl acrylate (95.0 g), ELVACITE™ 1020 polymethylmethacrylate macromonomer (12.5 g), VAZO 52 (0.5 g), ethyl acetate (356.25 g) and isopropyl alcohol (18.75 g) were charged into a one quart (0.95 L) bottle. The mixture was deoxygenated by purging with nitrogen (1 L/min) for 3 minutes. The bottle was sealed and placed in a rotating water bath at 45° C. for 24 hours. The bottle was removed, opened, charged with an additional 0.5 g of VAZO 52, repurged with nitrogen as before, sealed, and placed in the rotating water bath at 45° C. for an additional 24 hours. The percent solids of the resulting solution of copolymer was 39.2%. The inherent viscosity was 0.51 dl/g in ethyl acetate at 0.15 g/dl.

Preparation of Isooctyl Acrylate/Acrylamide (93/7) Copolymer

A reactor was charged with isooctyl acrylate (3500 g), acrylamide (263 g), methanol (614 g) and ethyl acetate (5,526 g). The mixture was deoxygenated and heated to 113° F. (45° C.). A solution of VAZO 52 (1.9 g) in ethyl acetate (150 g) was added when the temperature had stabilized at 113° F. (45° C.). Five and a half hours after the start of the reaction, a solution of VAZO 52 (1.9 g) in ethyl acetate (150 g) was added. Nine hours after the start of the reaction, a solution of VAZO 52(3.8 g) in ethyl acetate (150 g) was added. The reaction was continued at 113° F. (45° C.) until 98% minimum conversion was reached. The final polymer was diluted to 26–30% solids with ethyl acetate/methanol (90/10).

Preparation of "Dried" Adhesive

Dried adhesive is prepared by knife coating a 25 to 50 percent solids solution of the adhesive copolymer at a thickness of 10 to 25 mil (250 to 635 µM) onto a release liner. The coated release liner is oven dried to remove solvent and reduce the amount of residual monomers. The dried adhesive copolymer is stripped off the release liner and stored in a container.

In the examples that follow all percentages are weight/weight unless otherwise indicated. The weight percentages of the formulations after drying are calculated values and assume that only solvent was evaporated during the drying process.

EXAMPLE 1

Lauric acid (23.3 g), alfuzosin (23.3 g) and isopropyl myristate (6.67 g) were dissolved in warm (50° C.) ethanol (69.9 g, 96% ethanol with 4% water). Adhesive (26.67 g of dried 75/5/20 isooctyl acrylate/acrylamide/vinyl acetate, iv=1.3 dl/g) was dissolved in a mixture of ethyl acetate (56.09 g) and methanol (6.22 g). The two solutions were combined and mixed to provide a homogeneous coating formulation. The formulation was knife coated at a wet thickness of 350 µM onto a release liner (1022 SCOTCHPAK™ release liner from 3M Company). The coated release liner was oven dried for 30 minutes at 40° C. The resulting adhesive coating contained 29.15 percent alfuzosin, 29.15 percent lauric acid, 8.34 percent isopropyl myristate and 33.36 percent 75/5/20 isooctyl acrylate/acrylamide/vinyl acetate adhesive copolymer. The coated liner was then laminated onto a backing (1109 SCOTCHPAK™ polyester film laminate available from 3M Company). The laminate was die cut into 1.55 cm$^2$ patches. Penetration through hairless mouse skin was determined using the test method described above. The results are shown in the Table below where each value is the average of three independent determinations.

EXAMPLE 2

Lauric acid (21.54 g), alfuzosin (21.54 g) and isopropyl myristate (6.17 g) were dissolved in ethanol (64.62 g, 96% ethanol with 4% water). Adhesive (30.7 g of dried 57/38/5 isooctyl acrylate/hydroxyethyl acrylate/polymethylmethacrylate macromonomer (ELVACITE 1020) adhesive copolymer, iv=0.51 dl/g prior to drying) was dissolved in a mixture of ethyl acetate (26.1 g) and isopropanol (4.61 g). The two solutions were combined and mixed to provide a homogeneous coating formulation. The formulation was knife coated at a wet thickness of 315 µM onto a release liner (1022 SCOTCHPAK™ release liner from 3M Company). The coated release liner was oven dried for 30 minutes at 40° C. The resulting adhesive coating contained 26.94 percent alfuzosin, 26.94 percent lauric acid, 7.72 percent isopropyl myristate and 38.40 percent 57/38/5 isooctyl acrylate/hydroxyethyl acrylate/polymethylmethacrylate macromonomer adhesive copolymer. The coated liner was then laminated onto a backing (1109 SCOTCHPAK™ polyester film laminate available from 3M Company). The laminate was die cut into 1.55 cm$^2$ patches. Penetration through hairless mouse skin was determined using the test method described above. The results are shown in the Table below where each value is the average of three independent determinations.

EXAMPLE 3

Lauric acid (11.25 g), alfuzosin (11.25 g) and isopropyl myristate (3.21 g) were dissolved in ethanol (33.75 g, 96% ethanol with 4% water). Adhesive (12.87 g of dried 93/7 isooctyl acrylate/acrylamide, iv=1.32 dl/g in ethyl acetate at 0.15 g/dl) was dissolved in a mixture of ethyl acetate (61.76 g) and methanol (6.86 g). The two solutions were combined and mixed to provide a homogeneous coating formulation. The formulation was knife coated at a wet thickness of 400 µM onto a release liner (1022 SCOTCHPAK™ release liner from 3M Company). The coated release liner was oven dried for 30 minutes at 40° C. The resulting adhesive coating contained 29.16 percent alfuzosin, 29.16 percent lauric acid, 8.32 percent isopropyl myristate and 33.36 percent 93/7 isooctyl acrylate/acrylamide adhesive copolymer. The coated liner was then laminated onto a backing (1109 SCOTCHPAK™ polyester film laminate available from 3M Company). The laminate was die cut into 1.55 cm$^2$ patches. Penetration through hairless mouse skin was determined using the test method described above. The results are shown in the Table below where each value is the average of three independent determinations.

EXAMPLE 4

Lauric acid (23.3 g), alfuzosin (23.3 g), isopropyl myristate (6.67 g) and water free glycerol (3.2 g) were dissolved sequentially in warm (50° C.) ethanol (69.9 g, 96% ethanol/4% water). Adhesive (23.3 g of dried 75/5/20 isooctyl acrylate/acrylamide/vinyl acetate, I.V.=1.2 dl/g) was dissolved in a mixture of ethyl acetate (56.09 g) and methanol (6.22 g). The two solutions were combined and mixed to provide a homogeneous coating formulation. The formulation was knife coated at a wet thickness of 320 µm onto a suitable release liner (1–5 PESTR Matte 164Z from Daubert). The coated release liner was oven dried at 60° C. for 30 minutes. The resulting adhesive coating contained 29.14% alfuzosin, 29.14% lauric acid, 8.34% isopropyl myristate and 29.38% 73/7/20 isooctyl acrylate/acrylamide/vinyl acetate adhesive copolymer and 4.00% water free glycerol. The coated liner was then laminated to a backing film (e.g., Scotchpak™ 1109 polyester film laminate from 3M Company). The resulting laminate was die cut into 1.55 cm$^2$ patches. Penetration through hairless mouse skin was determined using the test method described above. The results are shown in the Table below where each value is the average of three independent determinations.

EXAMPLE 5

Lauric acid (13.98 g), glycerolmonolaurate (9.32 g), and alfuzosin base (23.3 g) were dissolved in ethanol (69.9 g, 96% ethanol, 4% water) at 50° C. Adhesive (28.87 g of dried 75/5/20 isooctyl acrylate/acrylamide/vinyl acetate, iv=1.3 dl/g) was dissolved in a mixture of ethyl acetate (56.09 g) and methanol (6.22 g). The two solutions were combined and mixed to provide a homogeneous coating formulation. The formulation was knife coated at a wet thickness of 350 μm onto a release liner (1–5 PESTR Matte 164Z from Danbert). The coated release liner was oven dried at 60° C. for 30 minutes. The resulting adhesive coating contained 31.8% alfuzosin, 19.1% lauric acid, 12.72% glycerol monolaurate and 36.4% 75/5/20 adhesive copolymer. The coated liner was then laminated onto a backing (1109 Scotchpak polyester film laminate available from 3M Company). The laminate was die cut into 1.55 cm² patches. Penetration through hairless mouse skin was determined using the test method described above. The results are shown in the table below where each value is the average of three independent determinations.

Hairless Mouse Skin Penetration

| Example Number | Cumulative Amount Penetrating (μg/cm²) | | | Flux[1] (μg/cm²/hr) |
| --- | --- | --- | --- | --- |
| | 12 hr | 24 hr | 48 hr | |
| 1 | 358 | 1018 | 1711 | 63 |
| 2 | 55 | 275 | 641 | 18 |
| 3 | 179 | 644 | 1242 | 35 |
| 4 | 333 | 1000 | 1690 | 47 |
| 5 | 407 | 948 | 1624 | 43 |

[1] 6–24 hours

What is claimed is:

1. A transdermal delivery device comprising:
   (A) a backing;
   (B) an adhesive layer adhered to one surface of the backing and comprising a combination of
      (1) a copolymer comprising
         (a) one or more A monomers selected from the group consisting of alkyl acrylates containing 4 to 10 carbon atoms in the alkyl group and alkyl methacrylates containing 4 to 10 carbon atoms in the alkyl group; and
         (b) one or more ethylenically unsaturated B monomers having a functional group selected from the group consisting of carboxylic acid, sulfonamide, urea, carbamate, carboxamide, hydroxy, amino, oxy, oxo, and cyano;
      (2) alfuzosin in an amount effective as an $a_1$-adrenoreceptor antagonist; and
      (3) a skin-penetration enhancing amount of a fatty compound selected from the group consisting of $C_8$–$C_{22}$ fatty acids, 1 to 4 carbon alkyl esters of $C_8$–$C_{22}$ fatty acids, and mixtures thereof.

2. A device according to claim 1, wherein the A monomer is selected from the group consisting of isooctyl acrylate, 2-ethylhexyl acrylate, butyl acrylate, and cyclohexyl acrylate.

3. A device according to claim 1, wherein the A monomer is isooctyl acrylate.

4. A device according to claim 1, wherein the B monomer is selected from the group consisting of acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, diacetone acrylamide, a dialkyl acrylamide having 1 or 2 carbon atoms in the alkyl group, N-vinyl-N-methyl acetamide, N-vinyl valerolactam, N-vinyl caprolactam, N-vinyl-2-pyrrolidone, glycidyl methacrylate, glyceryl acrylate, vinyl acetate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl methacrylate, furfuryl acrylate, tetrahydrofurfuryl acrylate, tetrahydrofurfuryl methacrylate, propylene glycol monomethacrylates, polyethylene oxide methyl ether acrylates, polyethylene glycol methyl ether acrylates, di(lower)alkylamino ethyl acrylate, di(lower)alkylamino ethyl methacrylate, di(lower)alkylaminopropyl methacrylamide, acrylonitrile, methacrylonitrile, and a mixture thereof.

5. A device according to claim 1, wherein the B monomer is selected from the group consisting of hydroxyethyl acrylate, hydroxyethyl methacrylate, glyceryl acrylate, N,N-dimethyl acrylamide, 2-ethoxyethoxyethyl acrylate, 2-ethoxyethyl acrylate, tetrahydrofurfuryl acrylate, acrylamide, vinyl acetate, acrylic acid, and a mixture thereof.

6. A device according to claim 1, wherein the B monomer is selected from the group consisting of hydroxyethyl acrylate, acrylamide, vinyl acetate, and a mixture thereof.

7. A device according to claim 1, wherein the alfuzosin is present in an amount of about 20 to about 40 percent by weight based on the total weight of the adhesive layer.

8. A device according to claim 1, wherein the alfuzosin is present in an amount of about 25 to 35 percent by weight based on the total weight of the adhesive layer.

9. A device according to claim 1, wherein the alfuzosin is dissolved in the adhesive layer.

10. A device according to claim 1, wherein the adhesive layer is substantially free of solid undissolved alfuzosin.

11. A device according to claim 1, wherein the A monomer is present in a total amount of 50 to 95 percent by weight, based on the total weight of all monomers in the copolymer.

12. A device according to claim 1, wherein the B monomer is present in a total amount of about 5 to about 40 percent by weight, based on the total weight of all monomers in the copolymer.

13. A device according to claim 1, wherein the fatty compound is dissolved in the adhesive layer.

14. A device according to claim 1, wherein the fatty compound is selected from the group consisting of lauric acid, caprylic acid, and isopropyl myristate.

15. A device according to claim 1, wherein the fatty compound is present in an amount of about 20 to 45 percent by weight based on the total weight of the adhesive layer.

16. A device according to claim 15, wherein the fatty compound is present in an amount of about 30 to 40 percent by weight based on the total weight of the adhesive layer.

17. A device according to claim 1, wherein the copolymer further comprises a substantially linear macromonomer copolymerizable with the A and B monomers and having a molecular weight in the range 500–500,000 in an amount of not more than about 30% by weight based on the total weight of the comonomers in the copolymer.

18. A device according to claim 17, wherein the macromonomer is present in an amount of not more than 15% by weight based on the total weight of all monomers in the copolymer.

19. A device according to claim 17, wherein the macromonomer is a polymethylmethacrylate macromonomer.

20. A method of treating in an animal a condition capable of treatment by alfuzosin, comprising the steps of:
   (i) providing a transdermal delivery device according to claim 1;
   (ii) applying the device to the skin of the animal; and
   (iii) allowing the device to remain on the skin for a time sufficient to establish or maintain a blood level of alfuzosin effective as an $α_1$-adrenoreceptor antagonist.

* * * * *